(12) United States Patent
Schwarz et al.

(10) Patent No.: US 12,311,410 B2
(45) Date of Patent: May 27, 2025

(54) PLANAR DRIVE APPARATUS AND METHOD FOR OPERATING A PLANAR DRIVE APPARATUS

(71) Applicant: Syntegon Technology GmbH, Waiblingen (DE)

(72) Inventors: Sebastian Schwarz, Neusitz (DE); Johannes Rauschnabel, Fichtenau (DE); Thomas Kosian, Insingen (DE)

(73) Assignee: Syntegon Technology GmbH, Waiblingen (DE)

( * ) Notice: Subject to any disclaimer, the term of this patent is extended or adjusted under 35 U.S.C. 154(b) by 190 days.

(21) Appl. No.: 18/353,496

(22) Filed: Jul. 17, 2023

(65) Prior Publication Data
US 2024/0025661 A1    Jan. 25, 2024

(30) Foreign Application Priority Data

Jul. 20, 2022  (DE) ..................... 10 2022 118 128.6

(51) Int. Cl.
  *B08B 1/20*  (2024.01)
  *A61L 2/26*  (2006.01)
  (Continued)

(52) U.S. Cl.
  CPC ................. *B08B 1/20* (2024.01); *A61L 2/26* (2013.01); *B08B 1/12* (2024.01); *B08B 3/02* (2013.01);
  (Continued)

(58) Field of Classification Search
  CPC .... B08B 1/20; B08B 1/12; B08B 3/02; B08B 3/022; A61L 2/26; B65G 54/02;
  (Continued)

(56) References Cited

U.S. PATENT DOCUMENTS 6,445,093 B1 * 9/2002 Binnard .............. G03F 7/70716
                                                            310/12.25
9,202,719 B2 * 12/2015 Lu ........................ H02K 1/2795
    (Continued)

FOREIGN PATENT DOCUMENTS

DE    102019117431 A1    12/2020
WO     2015179962 A1    12/2015
    (Continued)

OTHER PUBLICATIONS

European Patent Office Search Report for Application No. 23183720.4 dated Dec. 18, 2023 (14 pages including English translation).
(Continued)

*Primary Examiner* — Mark A Deuble
(74) *Attorney, Agent, or Firm* — Michael Best & Friedrich LLP

(57) ABSTRACT

A planar drive apparatus includes at least one mover and a drive table. The mover has an outer shell, the drive table has a planar drive surface, and the mover can be electromagnetically coupled to the drive surface and can be moved in a floating state parallel to the drive surface. The drive table has a cleaning region including a cleaning device for cleaning at least a part of the outer shell of the mover. The mover can be brought into the cleaning region by electromagnetic drive of the drive surface. The cleaning device has at least one additional cleaning unit which is arranged on or above the drive surface and which is configured to clean a side surface and/or a top side of the mover.

13 Claims, 4 Drawing Sheets

(51) Int. Cl.
  *B08B 1/12*     (2024.01)
  *B08B 3/02*     (2006.01)
  *B65G 54/02*    (2006.01)

(52) U.S. Cl.
  CPC .............. *B08B 3/022* (2013.01); *B65G 54/02* (2013.01); *H02K 2201/18* (2013.01)

(58) Field of Classification Search
  CPC ........ B65G 43/00; B65G 45/10; B65G 54/00; H02K 2201/18; H02K 41/02
  See application file for complete search history.

(56) References Cited

U.S. PATENT DOCUMENTS

| | | |
|---|---|---|
| 2017/0179805 A1 | 6/2017 | Lu |
| 2017/0320682 A1 | 11/2017 | Paweletz et al. |
| 2018/0148268 A1 | 5/2018 | Wipf et al. |
| 2019/0233220 A1* | 8/2019 | Ragan ................... B65G 45/10 |
| 2021/0184612 A1* | 6/2021 | Prüssmeier ............. H02P 25/06 |
| 2022/0032477 A2 | 2/2022 | Lu et al. |
| 2022/0131426 A1 | 4/2022 | Prussmeier |
| 2023/0318365 A1* | 10/2023 | Schwarz .................. H02K 1/12 |
| | | 310/12.15 |

FOREIGN PATENT DOCUMENTS

| | | |
|---|---|---|
| WO | 2016091444 A1 | 6/2016 |
| WO | 2022009476 A1 | 1/2022 |
| WO | WO-2024148442 A1 * | 7/2024 |

OTHER PUBLICATIONS

German Patent Office action for Application No. 10 2022 118 128.6 dated Apr. 20, 2023 (7 pages including statement of relevance).

* cited by examiner

PLANAR DRIVE APPARATUS AND METHOD FOR OPERATING A PLANAR DRIVE APPARATUS

BACKGROUND

The invention relates to a planar drive apparatus.

US 2022/0032477 A2 and DE 10 2019 117 431 A1 have disclosed planar drive apparatuses comprising a drive table and electromagnetically coupled movers. Such apparatuses can be used, for example, for transporting different items for transport and/or for arranging and operating work tools.

During the operation of such planar drive apparatuses, contamination of the outer shell of the movers can often occur. By way of example, matter can be taken up from the immediate surroundings of the apparatus, and/or spilt media from an item for transport adhere to the outer shell of the movers.

For a smooth sequence of operation, it is desirable to remove the contaminants from the outer shell of the movers.

SUMMARY

Proceeding therefrom, the invention is based on the object of specifying an apparatus and a method which enable simple cleaning of the outer shell of the movers, in particular during ongoing operation of the apparatus.

The arrangement of the cleaning device on the drive table makes it possible to utilize an inherent function of the apparatus—namely the movability of the mover—in order to bring the mover into the cleaning region and thus into direct spatial proximity to the cleaning device.

In this way, it is possible to integrate the cleaning of the outer shell of the mover into the sequence of operation. By way of example, during the movement between picking-up location and setting-down location of an item for transport, the mover can be brought into the cleaning region and be cleaned there, as a result of which the outlay in terms of time for the cleaning is minimized and in particular manual intervention can be dispensed with.

The apparatus is suitable in particular for use as part of a pharmaceutical installation. In such an installation, particularly high demands are placed on the cleanliness and sterility of the individual components and in particular of the outer shell of the movers.

In a preferred embodiment, the cleaning device has a cleaning unit which cooperates with a bottom side of the mover, said bottom side facing the drive surface. Owing to the fact that there is only a small spacing between the mover and the drive surface, the bottom side of the mover is particularly difficult to access for cleaning. Since the electromagnetic forces are also active between the drive surface and the bottom side of the mover, in particular magnetically active contaminants accumulate there. If the cleaning unit cooperates with the bottom side of the mover, contaminants can be removed therefrom in a targeted manner.

Particularly preferably, the drive surface has a plurality of tile-like drive portions, wherein a cleaning unit of the cleaning device is arranged in a gap formed between adjacent drive portions. The arrangement of the cleaning device in a gap between adjacent drive portions makes it possible to obtain the freedom of movement of the mover on the entire drive surface and to nevertheless provide a possibility for cleaning the outer shell of the mover. A preferred minimum gap width is 3 mm. A preferred maximum gap width is 60 mm. In particular, it is preferred for a gap width to not be greater than 30% of a length or of a width of a mover body (in each case measured parallel to the drive surface).

It is also preferred for the cleaning region to be delimited by the cleaning device at least in the direction of the drive surface. This ensures that the cleaning device is arranged as close as possible to the cleaning region and thus close to the outer shell of the mover, and at least the bottom side of the mover can be cleaned in a particularly effective manner.

According to the invention, the cleaning device has at least one additional cleaning unit which is arranged on or above the drive surface and which is intended to clean a side surface and/or a top side of the mover. This allows further partial regions of the outer shell or the entire outer shell of the mover to be cleaned in the cleaning region. In this case, the at least one additional cleaning unit may be arranged in such a way that simultaneous cleaning of the bottom side and of the side surface and/or top side of the mover is possible.

It is also preferred for the cleaning device to comprise at least one spray element for spraying a cleaning medium and/or a UV source. Spraying allows the cleaning medium to be applied to the outer shell of the mover in a targeted and particularly uniform manner. In this case, the number of spray elements may be matched to the width of the mover, in order to generate a particularly efficient spray pattern and to minimize the consumption of the cleaning medium. The use of the UV source represents a particularly effective possibility in relation to biological contaminants and can be combined with the spray elements in the cleaning device in a simple manner.

Furthermore, it is preferred for the cleaning device to comprise mechanical cleaning elements. Mechanical cleaning elements, for example brushes and/or sponges, make it possible to remove particularly stubborn contaminants. Preferably, the mover is brought into contact with the mechanical cleaning elements and moved relative to the stationary cleaning elements. It is also possible for the cleaning device to have a combination of mechanical cleaning elements and spray elements and/or the UV source.

In particular, it is preferred for the cleaning region to comprise a draining device and/or a suction-removal device. In this way, after cleaning is completed, a surplus of the cleaning medium and in particular a backflow of the cleaning medium can be removed from the drive table and collected in a simple manner.

It is also preferred for the draining device and/or the suction-removal device to be integrated into the cleaning device. This represents a simple possibility for applying and removing the cleaning medium in the cleaning space without requiring additional structural modifications to the drive table.

For the purpose of reducing the outlay in terms of time, it is particularly preferred for a plurality of movers to be able to be arranged and cleaned in the cleaning region at the same time.

The object mentioned in the introduction is also achieved by means of a method for operating a planar drive apparatus.

The method according to the invention provides for the mover to be arranged in the cleaning region and for at least a part of the outer shell of the mover to be cleaned by means of the cleaning device. In this case, it is possible for the mover to be stationary in the cleaning region or to be driven in such a way that the mover moves at a constant speed in the cleaning region.

The method makes it possible to integrate the cleaning of the outer shell of the mover into the sequence of operation and to minimize the expenditure of time for the cleaning.

According to a preferred method, the mover carries out a rotational movement about its vertical axis in the cleaning region. As a result, the cleaning medium and/or UV light is applied to the outer shell of the mover in a uniform manner.

It is also possible for the mover to carry out oscillating movements along and/or about its transverse axis and/or longitudinal axis and/or vertical axis in the cleaning region. The oscillating movement promotes a distribution of a cleaning medium on the outer shell of the mover.

Further features and advantages are the subject of the following description and of the diagrammatic illustration of embodiments.

DETAILED DESCRIPTION

Figure 1:
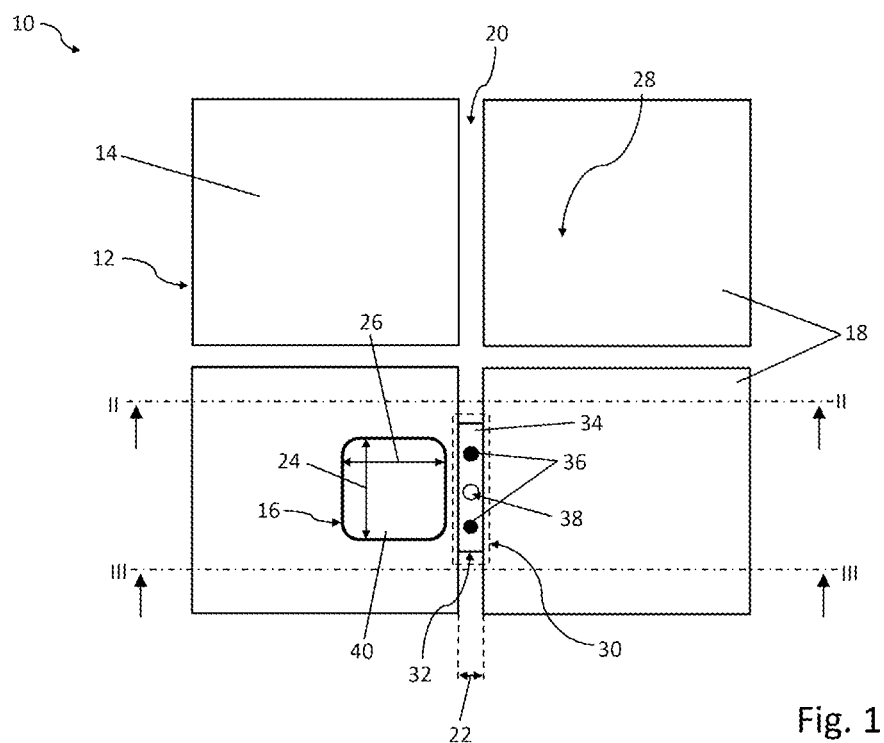
FIG. 1 shows a plan view of one embodiment of a planar drive apparatus comprising a mover and a drive surface with a cleaning region.

In the drawing, a planar drive apparatus is denoted as a whole by the reference sign 10. The planar drive apparatus 10 comprises a stationary drive table 12 with a planar drive surface 14 and a mover 16 which is electromagnetically coupled to the drive surface 14. The mover 16 can be driven and freely positioned in a floating state on the drive surface 14 (cf. FIG. 1).

Figure 2:
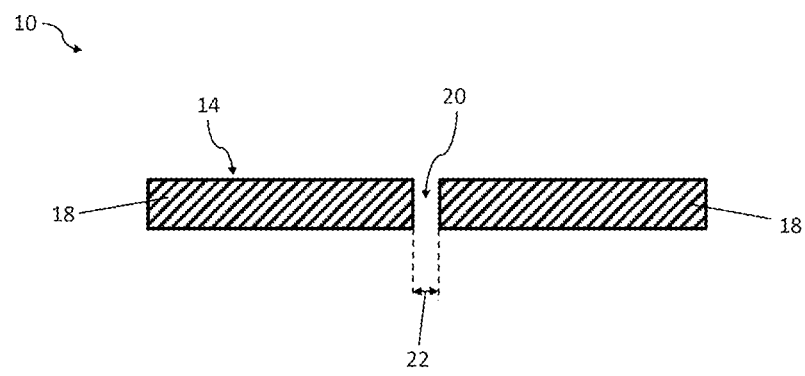
FIG. 2 shows a front view of the planar drive apparatus along a section plane denoted by II-II in FIG. 1.

The drive table 12 comprises a plurality of tile-like drive portions 18. The drive portions 18 are arranged in such a way that adjacent drive portions 18 are separated from one another by a gap 20 with a fixed gap width 22 (cf. FIGS. 1 and 2).

The mover 16 can be driven over the gap 20, wherein the gap width 22 is preferably considerably smaller than a width 24 or length 26 of the mover 16. By way of example, the width 22 of the gap 20 is not greater than 30% of the width 24 or of the length 26 of the mover 16.

The drive surface 14 has a work region 28. In the work region 28, the mover 16 can perform various work functions, for example transport an item for transport and/or interact with work tools (not illustrated).

The drive surface 14 also has a cleaning region 30. The cleaning region 30 extends, for example, between two adjacent drive portions 18, in particular along a partial length of a gap 20 in the drive surface 14. A cleaning device 32 comprising a cleaning unit 34 is arranged in the cleaning region 30 and delimits the cleaning region 30 in the direction of the drive surface 14.

The cleaning device 32 has spray elements 36 which are oriented perpendicularly with respect to the drive surface 14 and which are intended to spray a cleaning medium, and also optionally a draining device 38. It is also conceivable for one or more UV sources or a combination of spray elements 36 and UV sources to be arranged on the cleaning unit 34.

Figure 3:
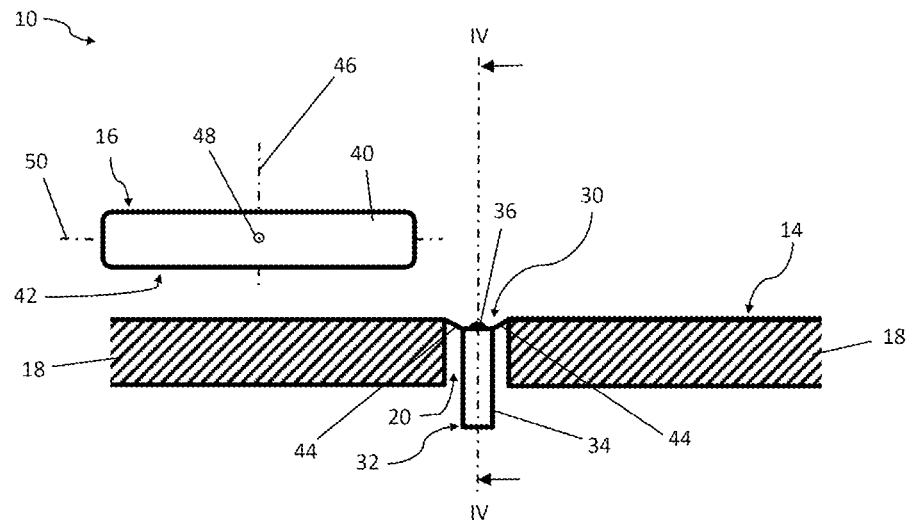
FIG. 3 shows a front view of the planar drive apparatus along a section plane denoted by III-III in FIG. 1, with the cleaning region in enlarged illustration.

The cleaning device 32 serves to clean at least a part of an outer shell 40 of the mover 16, in particular a bottom side 42 of the mover 16, said bottom side facing the drive surface (cf. FIG. 3).

The cleaning unit 34 is arranged set back in relation to the drive surface 14 of adjacent drive portions 18, wherein the offset is compensated by connecting profiles 44 whose top sides are inclined relative to the drive surface 14.

In order to clean the bottom side 42, the mover 16 is brought from the work region 28 into the cleaning region 30 by the electromagnetic drive of the drive surface 14, and the cleaning medium is applied to the bottom side 42 by the spray elements 36. In this case, the mover 16 may be stationary in the cleaning region 30 or may move at a constant speed through the cleaning region 30.

For a particularly uniform distribution of the cleaning medium, it is possible for the mover 16 to—in tandem with the stationary state or the constant movement—carry out a rotational movement about its vertical axis 46 and/or oscillating movements about and/or along its transverse axis 48 and/or longitudinal axis 50 and/or vertical axis 46.

Figure 4:
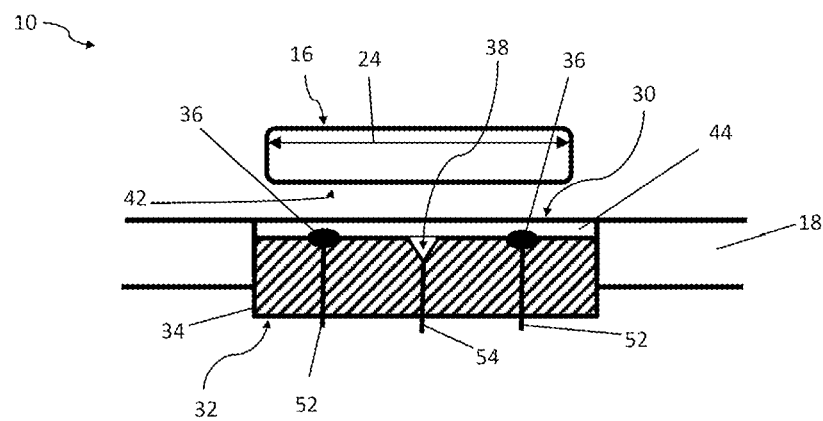
FIG. 4 shows a side view of the cleaning region along a section plane denoted by IV-IV in FIG. 3.

In order to use a cleaning medium as efficiently as possible, it is preferred for the number of spray elements 36 and the positioning and distribution thereof in the cleaning unit 34 to be matched to the width 24 and/or length 26 of the mover 16 (cf. FIG. 4 which shows a sectional illustration of the apparatus 10 along the section plane marked with IV-IV in FIG. 3). The spray elements 36 are connected, by way of lines 52, to a cleaning medium reservoir, which is not illustrated and which is preferably arranged in or on the drive table 12, and to a pump system and can preferably be actuated in groups or individually.

The draining device 38 is for example in the form of a centrally arranged, funnel-like depression in the cleaning unit 34. At its tapered end, the depression is connected to a drain line 54 running within the cleaning unit 34, as a result of which excess and returning cleaning medium, which may be provided with dirt from the mover 16, can be discharged from the drive surface 14.

Figure 5:
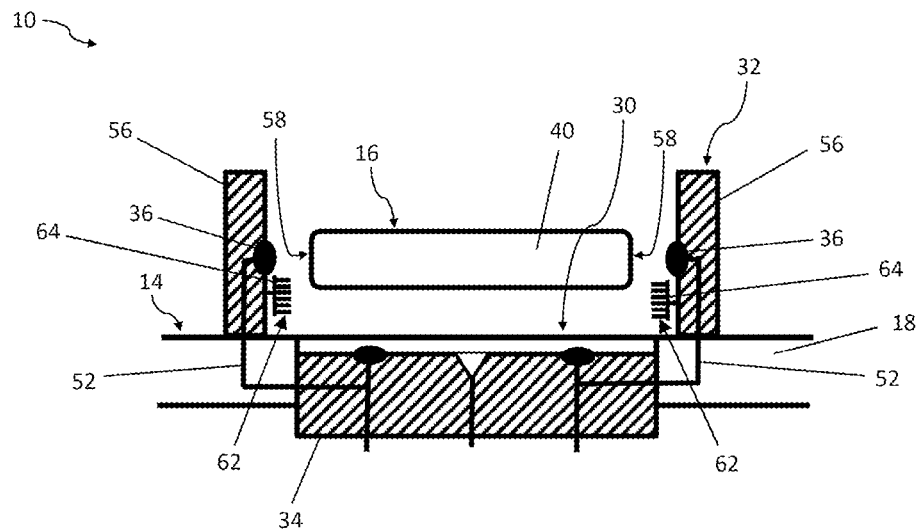
FIGS. 5 and 6 show views of the planar drive apparatus that correspond to FIG. 4 with additional cleaning units for cleaning side surfaces and/or top sides of the mover.
Figure 6:
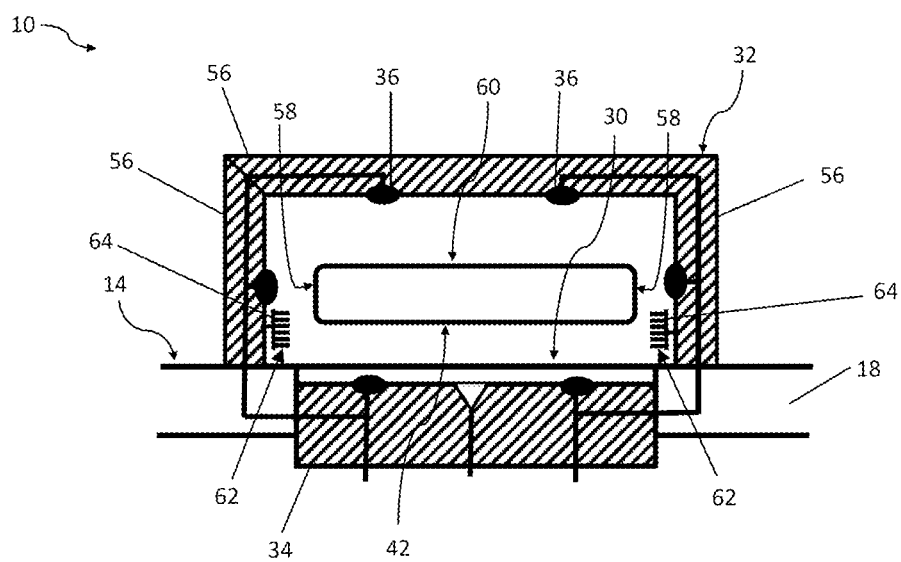

It is possible for the cleaning device 32 to be extended by one or more additional cleaning units 56 (cf. FIGS. 5 and 6). The additional cleaning units 56 are arranged on or above the drive surface 14 and form, for their part, a delimitation of the cleaning region 30. The additional cleaning units 56 are in particular arranged in such a way that simultaneous cleaning of the bottom side 42 and of side surfaces 58 and/or of a top side 60 of the mover 16 is possible.

In order to apply the cleaning medium to the outer shell 40 of the mover 16, the additional cleaning units 56 also have spray elements 36 and lines 52.

In addition to the spray elements 36, the cleaning unit 34 and/or the additional cleaning units 56 may comprise mechanical cleaning elements 62, for example brushes 64. For cleaning purposes, during and/or after application of the cleaning medium, the mover 16 is brought into contact with the mechanical cleaning elements 62 and moved relative to the mechanical cleaning elements 62.

Figure 7:
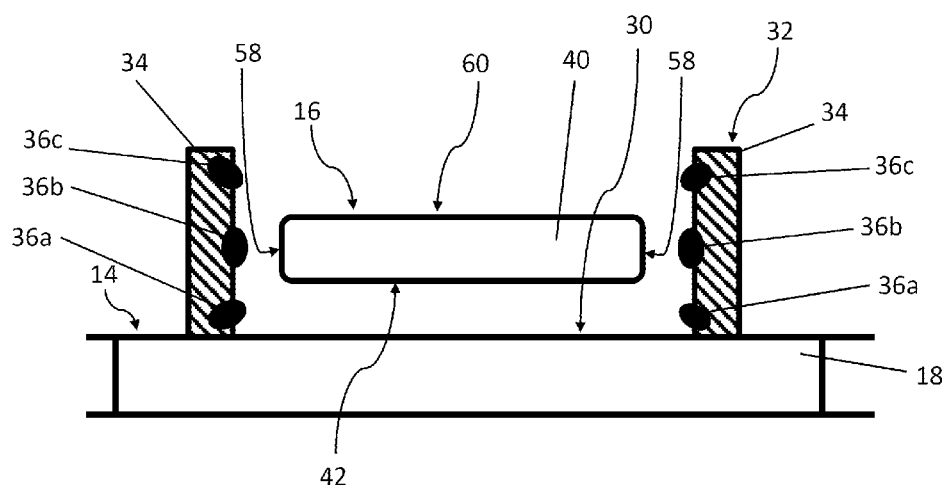
FIG. 7 shows a view of a further embodiment of a planar drive apparatus, said view corresponding to FIG. 4.

FIG. 7 shows a further embodiment of the planar drive apparatus 10 in a sectional illustration corresponding to FIGS. 4 to 6. In a deviation from the embodiment described above, the cleaning device 32 is not arranged in a gap between adjacent drive portions 18, but rather on or above the drive surface 14.

The cleaning device 32 comprises cleaning units 34 with spray elements 36a to 36c, which have different spraying directions. The spray elements 36a to 36c are arranged spaced apart with different spacings to the drive surface 14 and have preferably identical spacings relative to one another.

The cleaning units 34 have spray elements 36a which are arranged adjacent to the drive surface 14 and which spray the cleaning medium away from the drive surface 14 in the direction of the bottom side 42 of the mover 16 arranged in the cleaning region 30.

The cleaning units 34 have spray elements 36b which are at a further spacing to the drive surface 14 in relation to the spray elements 36a and which spray the cleaning medium in a direction parallel to the drive surface 14 onto the side surfaces 58 of the mover 16 arranged in the cleaning region 30.

The cleaning units 34 have spray elements 36c which are at a further spacing to the drive surface 14 in relation to the spray elements 36b and which spray the cleaning medium in the direction of the drive surface 14 onto the top side 60 of the mover 16 arranged in the cleaning region 30.

If the mover 16 is brought into the cleaning region 30, the arrangement according to FIG. 7 also makes it possible to clean the entire outer shell 40 of the mover 16, it not being necessary to arrange any cleaning units 34 below and/or above the drive surface 14 (i.e. in a deviation from the arrangements according to FIGS. 5 and 6).

The invention claimed is:

1. A planar drive apparatus (10) comprising at least one mover (16) and a drive table (12), wherein the mover (16) has an outer shell (40), wherein the drive table (12) has a planar drive surface (14) and wherein the mover (16) can be electromagnetically coupled to the drive surface (14) and can be moved in a floating state parallel to the drive surface (14), wherein the drive table (12) has a cleaning region (30) comprising a cleaning device (32) for cleaning at least a part of the outer shell (40) of the mover (16), wherein the mover (16) can be brought into the cleaning region by electromagnetic drive of the drive surface (14), wherein the cleaning device (32) has at least one additional cleaning unit (56) which is arranged on or above the drive surface (14) and which is configured to clean a side surface (58) and/or a top side (60) of the mover (16).

2. The planar drive apparatus (10) according to claim 1, wherein the cleaning device (32) has a cleaning unit (34) which cooperates with a bottom side (42) of the mover (16), said bottom side facing the drive surface (14).

3. The planar drive apparatus (10) according to claim 1, wherein the drive surface (14) has a plurality of tile-like drive portions (18), and wherein a cleaning unit (34) of the cleaning device (32) is arranged in a gap (20) formed between adjacent drive portions (18).

4. The planar drive apparatus (10) according to claim 1, wherein the cleaning region (30) is delimited by the cleaning device (32) at least in a direction of the drive surface (14).

5. The planar drive apparatus (10) according to claim 1, wherein the cleaning device (32) comprises at least one spray element (36) for spraying a cleaning medium and/or a UV source.

6. The planar drive apparatus (10) according to claim 1, wherein the cleaning device (32) comprises mechanical cleaning elements (62).

7. The planar drive apparatus (10) according to claim 1, wherein the cleaning region (30) comprises a draining device (38) and/or a suction-removal device.

8. The planar drive apparatus according to claim 7, wherein the draining device (38) and/or suction-removal device is integrated into the cleaning device (32).

9. The planar drive apparatus (10) according to claim 1, wherein a plurality of movers (16) can be arranged and cleaned in the cleaning region (30) at the same time.

10. A method for operating a planar drive apparatus (10) according to claim 1, wherein the mover (16) is arranged in the cleaning region (30) and wherein at least a part of the outer shell (40) of the mover (16) is cleaned by the cleaning device (32), wherein, during the cleaning, the mover (16) is stationary in the cleaning region (30), or is driven in such a way that the mover (16) moves at a constant speed in the cleaning region (30).

11. The method according to claim 10, wherein the mover (16) carries out a rotational movement about its vertical axis (46) in the cleaning region (30).

12. The method according to claim 10, wherein the mover (16) carries out oscillating movements along and/or about its transverse axis (48) and/or longitudinal axis (50) and/or vertical axis (46) in the cleaning region (30).

13. The method according to claim 11, wherein the mover (16) carries out oscillating movements along and/or about its transverse axis (48) and/or longitudinal axis (50) and/or vertical axis (46) in the cleaning region (30).

* * * * *